United States Patent [19]

Kiehs et al.

[11] 4,192,831

[45] Mar. 11, 1980

[54] MANUFACTURE OF SALTS OF O,S-DITHIOPHOSPHORIC ACIDS

[75] Inventors: Karl Kiehs, Lampertheim; Hans Theobald, Limburgerhof, both of Fed. Rep. of Germany

[73] Assignee: BASF Aktiengesellschaft, Fed. Rep. of Germany

[21] Appl. No.: 836,062

[22] Filed: Sep. 23, 1977

Related U.S. Application Data

[63] Continuation-in-part of Ser. No. 655,457, Feb. 5, 1976, abandoned.

[30] Foreign Application Priority Data

Feb. 17, 1975 [DE] Fed. Rep. of Germany ....... 2506618

[51] Int. Cl.$^2$ .............................................. C07F 9/165

[52] U.S. Cl. ..................................... 260/987; 260/925
[58] Field of Search .......................... 260/925; 261/987

[56] References Cited

U.S. PATENT DOCUMENTS

| | | | |
|---|---|---|---|
| 3,518,261 | 6/1970 | Nguyen et al. | 260/945 X |
| 3,662,034 | 5/1972 | Oswald et al. | 260/987 X |
| 3,812,217 | 5/1974 | Moyer | 260/925 X |
| 3,845,171 | 10/1974 | Beriger | 260/925 X |
| 3,904,710 | 9/1975 | Oswald et al. | 260/987 X |

*Primary Examiner*—Anton H. Sutto
*Attorney, Agent, or Firm*—Keil & Witherspoon

[57] ABSTRACT

A new process for the manufacture of ammonium salts of O,S-dithiophosphoric acid esters by reaction of an O,O,S-dithiophosphoric acid triester with an amine.

7 Claims, No Drawings

MANUFACTURE OF SALTS OF O,S-DITHIOPHOSPHORIC ACIDS

This application is a continuation-in-part of our patent application Ser. No. 655,457 filed Feb. 5, 1976, now abandoned.

The present invention relates to a new process for the manufacture of ammonium salts of O,S-dithiophosphoric acid esters. Such salts are important starting materials for the preparation of symmetrical and unsymmetrical O,S,S-dithiophosphoric triesters, which are valuable pesticidal, for example insecticidal, nematicidal and fungicidal active compounds.

Various processes for the manufacture of salts of O,S-dithiophosphoric acid diesters have been disclosed. Thus, eg., the reaction of O,O,S-dithiophosphoric acid triesters with alkali metal mercaptides in anhydrous alcohol according to German Pat. No. 1,100,019 gives alkali metal salts of O,S-dithiophosphoric acid diesters. The process takes place in accordance with equation (I) given below by way of example:

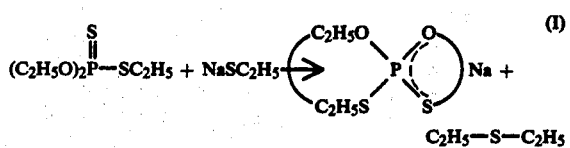

The reaction of O,O,S-dithiophosphoric acid triesters with potassium xanthate has also been disclosed, in German Patent No. 1,141,634. This takes place in accordance with equation (II) given below by way of example:

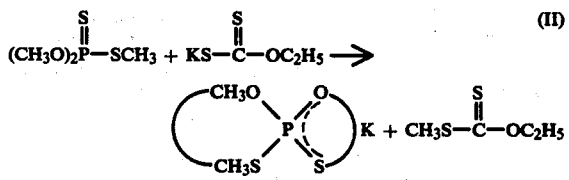

The reaction of O,O,S-dithiophosphoric acid triesters with alkali metal bisulfides has also been disclosed, in German Printed Application No. 1,768,141, and takes place in accordance with equation (III), given below by way of example:

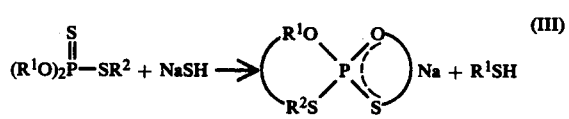

In this equation $R^1$ is alkyl and $R^2$ is alkyl, phenyl or phenylalkyl.

Belgian Patent No. 600,635 discloses the reaction of O,O,S-dithiophosphoric acid triesters with potassium salts of an O,O-dithiophosphoric acid diester, in accordance with equation (IV) given below by way of example:

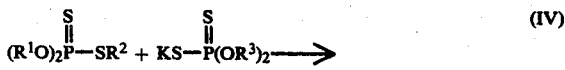

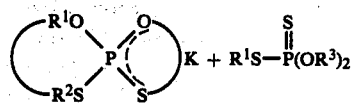

In this equation, $R^1$, $R^2$ and $R^3$ are identical or different alkyl.

It is also known that O,O,S-dithiophosphoric acid triesters react with primary amines in organic solvents, over periods of several days, to give the corresponding alkylammonium salts, in accordance with equation (V) given below. However, this reaction only takes place if $R^1$ is methyl, $R^2$ and $R^3$ being alkyl. (Houben-Weyl, Methoden der organischen Chemie, volume 12/2, page 690, Georg-Thieme-Verlag, Stuttgart, 1964; N. N. Melnikow et al., J. Gen. Chem. USSR 31, 3361 (1961), 32, 1818, 2816 (1962); reviewed in C. A. 57, 11071 (1962), 58, 4456, 12,402 (1963)).

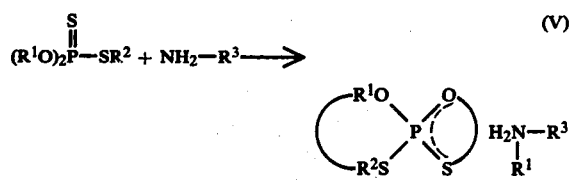

British Patent No. 1,287,621 discloses the reaction of O,O,S-dithiophosphoric acid triesters with amines, eg. with $NH_3$ or $N(CH_3)_3$ in the absence of solvents, or with triethylenediamine in organic solvents, resulting in the corresponding ammonium salts of the O,S-dithiophosphoric acid diesters being produced, in moderate yields only, over reaction times of from 1 to 3 days. The reactions take place in accordance with equations (VI) and (VII) below:

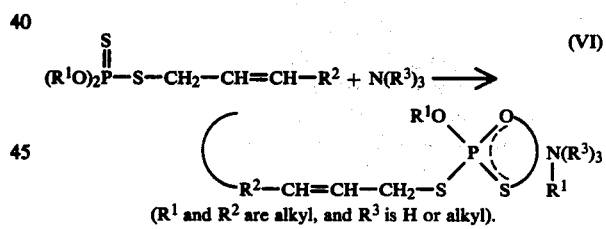

($R^1$ and $R^2$ are alkyl, and $R^3$ is H or alkyl).

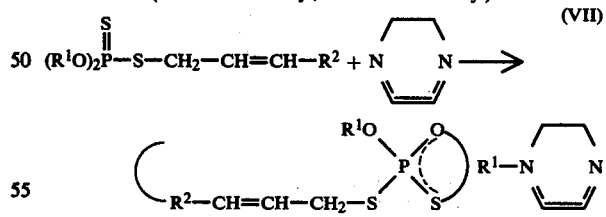

However, the conventional processes have the following disadvantages:

1. In the processes of German Patent No. 1,100,019, Belgian Patent 600,635 and German Printed Application No. 1,768,141, the manufacture of the starting compounds used, namely sodium mercaptides, potassium salts of O,O-dithiophosphoric acid diesters and alkali metal bisulfides, is involved and expensive.

2. The processes of German Patent No. 1,141,634 and British Patent No. 1,287,621 can only be carried out with expensive reagents such as potassium xanthate and 1,4-diazabicyclo-(2,2,2)-octane and therefore prove to be expensive and uneconomical.

3. In the processes of German Patent No. 1,100,019, German Patent No. 1,141,634 and German Printed Application No. 1,768,141 equimolar amounts of by-products such as thioethers, alkyl xanthates and mercaptans are formed, which severely pollute the environment and have an objectionable odor and therefore necessitate expensive and involved purification of the reaction products and off-gases.

4. In the processes of German Patent No. 1,411,634 and Belgian Patent No. 600,635, the after-treatment and working up of the reaction mixture in order to isolate the desired alkali metal salts of the dithiophosphoric acid diesters is difficult, involved and time-consuming.

5. In the processes of German Patent No. 1,100,019, German Patent No. 1,141,634, Belgian Pat. No. 600,635 and German Printed Application No. 1,768,141, reaction temperatures above 60°–70° C. are used. However, it is known that O,O,S-dithiophosphoric acid triesters easily isomerize to O,S,S-dithiophosphoric acid triesters even at moderately elevated temperatures and can then no longer be converted to the desired O,S-dithiophosphoric acid diesters (cf. Houben-Weyl, Methoden der organischen Chemie, volume 12/2, page 668, Georg-Thieme-Verlag, Stuttgart, 1964). Accordingly, the salts of the O,S-dithiophosphoric acid diesters can only be prepared in a highly impure state, and in moderate yields, by these processes.

6. The process of N. N. Melnikow, which corresponds to equation (V), only occurs satisfactorily if at least one substituent ($R^1$) on the oxygen is a methyl group. Even with $R^1$=ethyl, the reaction no longer takes place (cf. Houben-Weyl, Methoden der organischen Chemie, volume 12/2, page 690, Georg-Thieme-Verlag, Stuttgart, 1964). The extremely long reaction times, of from 2 to 3 days, mean that this process is of no interest for industrial application.

7. Accordingly to British Patent No. 1,287,621, amines such as ammonia, trimethylamine and triethylenediamine are used for salt formation. The patent itself describes an involved procedure using ammonia and trimethylamine, which must first be condensed in the reaction flask. The method gives only moderate yields, with reaction times of 2 days. Forming the salts with triethylenediamine also requires reaction times of about 24 hours and furthermore triethylenediamine is a very expensive reagent and uneconomical to use industrially.

It is an object of the present invention to provide a process which is simple to carry out industrially and which permits the manufacture of salts of O,S-dithiophosphoric acid diesters from cheap starting materials, without pollution of the environment, and with short reaction times and high yields, so that all disadvantages of the prior art processes are avoided.

We have found that this object is achieved when salts of O,S-dithiophosphoric acid diesters of the formula I

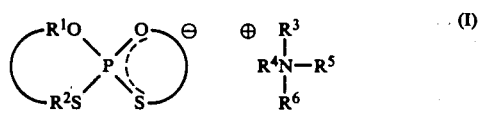

where $R^1$, $R^2$, $R^3$ and $R^6$ independently of one another are an organic radical and $R^4$ and $R^5$ independently of one another are hydrogen or an organic radical, are produced by reaction of an O,O,S-dithiophosphoric acid derivative of the formula II

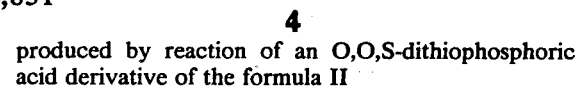

where $R^1$, $R^2$ and $R^3$ have the above meanings, with a compound of the formula III $$NR^4R^5R^6 \qquad (III)$$

where $R^4$, $R^5$ and $R^6$ have the above meanings, in the presence of water. The salts are obtained in a simple manner, free from isomers and in high—in most cases quantitative—yields.

$R^1$ to $R^6$ are preferably alkyl of 1 to 6 carbon atoms, alkenyl of 2 to 6 carbon atoms, alkynyl of 3 to 6 carbon atoms, alkoxyalkyl of 2 to 6 carbon atoms, alkylthioalkyl of 2 to 6 carbon atoms, phenyl or phenyl substituted by alkyl of up to 4 carbon atoms, halogen or haloalkyl, benzyl or benzyl substituted on the phenyl nucleus by alkyl of up to 4 carbon atoms, halogen or haloalkyl, or cycloalkyl of 6 to 8 carbon atoms, and $R^5$ and $R^6$, together with the nitrogen atom whose substituents they are, may form a heterocyclic ring having 6 members.

Preferred substitutents for $R^1$, $R^2$ and $R^3$ are alkyl of 1 to 4 carbon atoms, particularly methyl, ethyl and propyl, propargyl, butyn-2-yl, alkoxyalkyl of up to 4 carbon atoms, particularly methoxymethyl, 2-methoxyethyl and 2-methoxy-n-propyl, or benzyl. Preferred substituents for $R^4$ and $R^5$ are hydrogen or alkyls of 1 to 4 carbon atoms, particularly methyl and ethyl. Preferred substituents for $R^6$ are alkyls of 1 to 4 carbon atoms, particularly methyl and ethyl.

$R^1$ and $R^2$ are, eg., non-cyclic or cyclic, branched or unbranched, substituted or unsubstituted alkyl, alkenyl or alkynyl, substituted or unsubstituted phenyl or phenylalkyl, or non-cyclic or cyclic radicals containing hetero-atoms. Non-cyclic radicals containing hetero-atoms may be, eg., alkoxyalkyl or alkylthioalkyl. Preferred radicals $R^1$ and $R^2$ are methyl, ethyl, n-propyl, i-propyl, the butyl isomers, the hexyl isomers, allyl, the butenyl isomers, the hexenyl isomers, propargyl, the butynyl isomers, the pentynyl isomers, the hexynyl isomers, methoxymethyl, 2-methoxyethyl, 2-ethoxyethyl, 2-methoxypropyl, 3-ethoxypropyl, methylthiomethyl, 2-methylthioethyl, 2-ethylthioethyl, phenyl, phenyl substituted by alkyl of at most 4 carbon atoms, by halogen or by haloalkyl, benzyl, benzyl substituted in the phenyl nucleus by alkyl of at most 4 carbon atoms, by halogen or by haloalkyl, cyclohexyl, cycloheptyl and cyclooctyl. $R^3$, $R^4$, $R^5$ and $R^6$ are, eg., straight-chain or branched substituted or unsubstituted alkyl, alkenyl or alkynyl, phenyl or phenylalkyl and $R^5$ and $R^6$ together with the nitrogen can form a 6-membered heterocyclic ring, eg. a pyrrolidine, piperidine, morpholine, piperazine or other heterocyclic ring.

The O,O,S-dithiophosphoric acid derivatives employed as starting compounds can easily be manufactured by conventional processes (Houben-Wyel, Methoden der organischen Chemie, volume 12/2, page 692, Georg-Thieme-Verlag, Stuttgart, 1964).

To prepare the salts of the O,S-dithiophosphoric acid diesters from O,O,S-dithiophosphoric acid derivatives according to the invention it is possible in principle to use any primary, secondary or tertiary amine, i.e. a compound of the formula III, eg. in aqueous solution. These amines include the unbrached and branched primary aliphatic amines, eg. methylamine, ethylamine, propylamine, isopropylamine and the like, secondary aliphatic amines, eg. dimethylamine, methylethylamine, diethylamine, ethylpropylamine and the like, and tertiary amines, eg. trimethylamine, diethylmethylamine, triethylamine and the like. Cheap industrial-grade aqueous solutions of these amines are particularly interesting and suitable for this application. Higher aliphatic amines, eg. obtained as industrial by-products, can also be used for the salt formation; furthermore, these amines need not be single substances and it is perfectly possible to use mixtures of amines for the salt formation.

It is also possible to use alkanolamines, eg. ethanolamine, cyclic amines, eg. pyrrolidine, methylpyrrolidine, piperidine, morpholine and methylmorpholine, amines with two or more amino groups, eg. alkylenediamines or piperazine, or aromatic and aliphatic-aromatic amines, eg. aniline, alkylanilines, toluidines, benzylamines and the like, for the preparation of the salts of the O,S-dithiophosphoric acid diesters. Mixtures of these amines may also be used.

It is essential that the preparation of the ammonium salts of the O,S-dithiophosphoric acid diesters from O,O,S-dithiophosphoric acid derivatives should be carried out in the presence of water as the reaction medium.

However, it is also possible, especially in the case of amines which are sparingly soluble or insoluble in water, to add a solubilizing agent which both dissolves in water and also dissolves the amine itself. Examples of such solubilizing agents are alcohols, eg. methanol, ethanol and propanol, polyhydric alcohols, eg. glycol, substituted alcohols, eg. alkylene chlorohydrins, ethanolamines and the like, ethers, eg. dioxane and tetrahydrofuran, nitriles, eg. acetonitrile, ketones, eg. acetone and methyl ethyl ketone, dimethyl sulfoxide, dimethyl formamide and other solvents.

Preferred solubilizing agents are alcohols, particularly ethanol, ethers, particularly dioxane, ketones, nitriles, dimethyl sulfoxide and dimethyl formamide.

The preparation of the ammonium salts of the O,S-dithiophosphoric acid diesters with aqueous amine solutions can be carried out at temperatures ranging from the freezing point to the boiling point of the aqueous amine solutions; the preferred reaction temperatures are 0°–60° C.

The process according to the invention can be carried out under atmospheric pressure or superatmospheric pressure.

Aqueous amine solutions which can be used range from 1 percent strength by weight solutions to saturated solutions or, when working under superatmospheric pressure, even supersaturated solutions.

The aqueous amine solutions can be reacted with the O,O,S-dithiophosphoric acid derivatives in equimolar ratios, eg. if the reactions are carried out with aqueous solutions of tertiary amines. In that case, the reactions take place in accordance with equation (VIII). However, in the process according to the invention it is not essential for the amine solutions and O,O,S-dithiophosphoric acid derivatives to be employed in equimolar ratios for the reaction. If, eg., twice the molar amount, or even more, of aqueous primary or secondary amine solutions is reacted with O,O,S-dithiophosphoric acid derivatives, the reactions take place in accordance with equation IX.

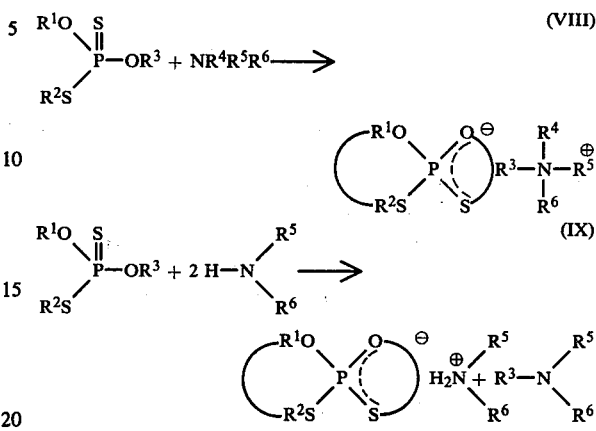

In these formulae, $R^1$, $R^2$, $R^4$ and $R^6$ are any organic radicals, eg. cyclic or non-cyclic alkyl, alkenyl or alkynyl, alkoxyalkyl or alkylthioalkyl, substituted or unsubstituted phenyl or phenylalkyl, or any cyclic or non-cyclic compounds containing heteroatoms, $R^3$ is, eg., unbranched or branched alkyl of up to 6 carbon atoms, $R^5$ is hydrogen or any organic radicals, eg. straight-chain or branched, substituted or unsubstituted, alkyl, alkenyl or alkynyl, phenyl or phenylalkyl, and $R^5$ and $R^6$ together with the nitrogen can form a heterocyclic ring, eg. a pyrrolidine, piperidine, morpholine, piperazine or other heterocyclic ring, provided that in equation VIII $R^5$ is not hydrogen.

The process according to the invention is suitably carried out by dropwise addition of an O,O,S-dithiophosphoric acid ester to an amine solution at 0°–60° C., any exothermic reaction being kept down to 60° C. In most cases, carrying out the reaction at 15°–30° C. suffices to achieve quantitative salt formation, without formation of isomers. In some cases it is necessary to continue the reaction for some time at 50°–55° C., a period of 3–6 hours having proved adequate in most cases. The end of the reaction is in most cases detectable from the disappearance of the turbidity caused by the O,O,S-dithiophosphoric acid ester employed. By removing the water and the solvent—where one is used—pure O,S-dithiophosphate salts are obtained. In most cases further purification is superfluous. The aqueous solutions of the O,S-dithiophosphate salts can in many cases be used as obtained, eg. for reaction with organic halogen compounds to give O,S,S-dithiophosphoric acid triesters.

The reaction with the aqueous solution of a secondary aliphatic amine, especially dimethylamine, is preferred.

The present invention thus provides a process which is particularly simple to carry out industrially, which uses cheap starting materials and short reaction times, usually gives quantitative yields, and permits the preparation of salts of O,S-dithiophosphoric acid diesters in the presence of water as a reaction medium, and without pollution of the environment.

The Examples which follow illustrate the process according to the invention.

EXAMPLE 1

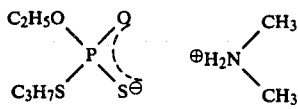

9 kg of O,O-diethyl-S-propylphosphorodithioate were added to 20 liters of 40% strength by weight aqueous dimethylamine solution at 20° C. and the mixture was then stirred for 6 hours at 50°-55° C. This gave a clear solution which was treated with 4 liters of toluene at 20° C. The aqueous phase was separated off and concentrated in a circulatory evaporator. 9.75 kg (=99% yield) of salt I were obtained as a pale yellow oil. $C_7H_{20}NPO_2S_2$ (245)

Analysis:

Calculated: C 34.3; H 8.2; N 5.7; P 12.7; S 26.1; Found: C 34.6; H 8.2; N 5.6; P 12.3; S 26.7.

100 Mc/s NMR spectrum (solvent: $D_2O$): δ values. 0.96 (3H), 1.28 (3H), 2.61 (2H), 2.74 (6H), 2.8 (2H), 3.97 (2H).

EXAMPLE 2

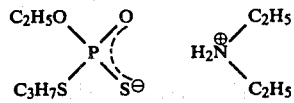

228 g of O,O-diethyl-S-propylphosphorodithioate were added to 366 g of a 40% strength aqueous diethylamine solution at 20° C. and the mixture was then stirred for 6 hours at 55° C.; thereafter it was extracted by shaking with 3 times 200 ml of ether and the water phase was concentrated and dried in a desiccator over $P_2O_5$. The salt II was obtained in the form of a pale yellow oil.

Yield: 255 g (93%).

$C_9H_{24}NPO_2S_2$ (273)

Calculated: C 39.6; H 8.3; N 5.1; P 11.4; S 23.4. Found: C 39.3; H 8.9; N 5.4; P 11.1; S 22.9.

100 Mc/s NMR spectrum (solvent: $CDCl_3$): δ-values. 0.96 (3H), 1.30 (3H), 1.43 (6H), 1.66 (2H), 2.74 (2H), 3.02 (4H), 3.98 (2H).

EXAMPLE 3

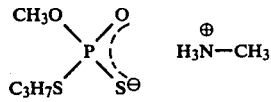

150 ml of 40% strength aqueous methylamine solution and 30 g of O,O-dimethyl-S-propylphosphorodithioate were stirred for 4 hours at 40° C. After cooling, the mixture was extracted by shaking with twice 100 ml of ether and the water phase was concentrated and subjected to incipient distillation at 50° C./0.1 mm Hg. 32 g (98%) of a pale yellow oil were obtained.

$C_5H_{16}O_2S_2PN$ (217)

Calculated: C 27.6; H 7.4; N 6.4; S 29.5; P 14.3. Found: C 28.0; H 7.6; N 6.7; S 28.9; P 13.8.

60 Mc/s NMR spectrum (solvent: $D_2O$): δ-values. 0.95 (3), 1.55 (2), 2.65 (3), 2.70 (2), 3.6 (3).

EXAMPLE 4

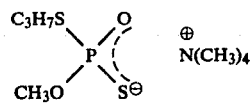

30 g of O,O-dimethyl-S-propylphosphorodithioate and 150 ml of 35% strength aqueous trimethylamine solution were stirred for 2 hours at 40° C., cooled and extracted by shaking with twice 100 ml of ether. The water phase was concentrated and subjected to incipient distillation at 45° C./0.1 mm Hg.

Yield: 37.4 g (96%) of a pale yellow oil.

$C_8H_{22}O_2S_2PN$ (259)

Calculated: C 37.0; H 8.5; N 5.4; S 24.7; P 11.9; Found: C 36.6; H 8.5; N 5.9; S 24.6; P 11.7.

60 Mc/s NMR spectrum (solvent: $D_2O$): δ-values. 0.95 (3H), 1.68 (2H), 2.7 (2H), 3.15 (12H), 3.6 (3H).

EXAMPLE 5

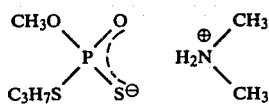

9.7 kg of O,O-dimethyl-S-propylphosphorodithioate are added dropwise to 20 liters of a 40% strength aqueous dimethylamine solution at 20° C., whereupon a slightly exothermic reaction occurs. The mixture was stirred for a further hour at 20° C. and then concentrated in a circulatory evaporator at 40° C./0.1 mm Hg.

Yield: 11.2 kg (100%) of a pale yellow oil.

$C_6H_{18}NPO_2S_2$ (231)

Calculated: C 31.2; H 7.8; N 6.1; P 13.4; S 27.7; Found: C 30.8; H 8.1; N 6.5; P 13.0; S 27.5.

100 Mc/s NMR spectrum (solvent: $D_2O$): δ-values. 0.97 (3H), 1.76 (2H), 2.74 (2H), 2.79 (6H), 3.67 (3H).

EXAMPLE 6

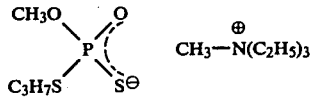

15.2 g of triethylamine, dissolved in 100 ml of water and 50 ml of dioxane, and 30 g of O,O-dimethyl-S-propylphosphorodithioate were stirred for 3 hours at 50° C. The solvents were then stripped off and the oil which remained was triturated with 100 ml of ether. The undissolved oil was separated off and subjected to incipient distillation at 45° C./1 mm Hg.

Yield: 38.5 g (96.4%) of a pale oil.

$C_{11}H_{28}O_2PS_2N$ (301)

Calculated: C 43.8; H 9.4; N 4.6; S 21.3; P 10.3; Found: C 43.6; H 8.9; N 4.9; S 20.8; P 10.3.

60 Mc/s NMR spectrum (solvent: $D_2O$): δ-values. 0.95 (3H), 1.3 (9H), 1.65 (2H), 2.67 (2H), 2.95 (3H), 3.36 (6H), 3.58 (3H).

The salts of the general formula

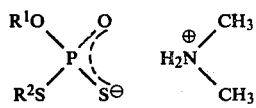

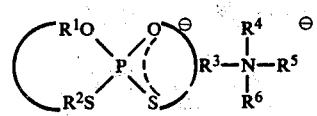

shown in the Table which follows were obtained analogously.

where $R^1$, $R^2$ and $R^6$ independently of one another denote an organic radical, $R^3$, $R^4$ and $R^5$ independently

| $R^1$ | $R^2$ | NMR Data (δ -values) |
| --- | --- | --- |
| $CH_3$ | $-CH_2-\bigcirc$ | 2.86 (2H); 3.55 (3H); 4.06 (2H); 7.05–7.4 (5H). $D_2O$/60 Mc/s |
| $C_2H_5$ | $C_4H_9$-n | 0.9 (3H); 1.31 (3H); 1.26–1.75 (4H); 2.81 (6H); 2.68 (2H); 4.04 (2H). $D_2O$/100 Mc/s |
| $C_2H_5$ | $C_3H_7$-i | 1.28 (3H); 1.36 (6H); 2.78 (6H); 3.3 (1H); 3.95 (2H). $D_2O$/60 Mc/s |
| $C_2H_5$ | $C_2H_5$ | 1.18–1.42 (6H); 2.78 (6H); 2.81 (2H); 4.02 (2H). $D_2O$/100 Mc/s |
| $CH_3$ | $C_4H_9$-n | 0.91 (3H); 1.2–1.82 (4H); 2.81 (6H); 2.83 (2H); 3.67 (3H). $D_2O$/100 Mc/s |
| $CH_3$ | $C_2H_5$ | 1.31 (3H); 2.79 (6H); 2.81 (2H); 3.68 (3H). $D_2O$/100 Mc/s |
| $CH_3$ | $CH_3$ | 2.2 (3H); 2.76 (6H); 3.67 (3H). $D_2O$/100 Mc/s |
| $C_2H_5$ | $CH_3$ | 1.31 (3H); 2.25 (3H); 2.79 (6H); 4.05 (2H). $D_2O$/100 Mc/s |
| $C_3H_7$ | $C_3H_7$ | 0.91 (3H); 0.93 (3H); 1.45–1.86 (4H); 2.74 (6H); 2.71 (2H); 3.88 (2H); 3.68 (3H). |
| $CH_3$ | $CH_2-C\equiv CH$ | 2.36 (1H); 2.86(6H); 3.57 (2H); 3.68 (3H). $CDCl_3$/100 Mc/s |
| $CH_3$ | $CH_2-CH=CH_2$ | 2.68 (6H); 3.37 (2H); 3.56 (3H); 5.13 (2H); 5.58–6.17 (1H). $D_2O$/60 Mc/s |
| $CH_3$ | $CH_2-C\equiv C-CH_3$ | 2.83 (3H); 2.72 (6H); 3.39 (2H); 3.6 (3H). $D_2O$/100 Mc/s |
| $\bigcirc-$ | $C_3H_7$ | |
| $\bigcirc-CH_2-$ | $C_3H_7$ | |
| $CH_3$ | $CH_2-CH_2-OCH_3$ | |
| $C_2H_5$ | $CH_2-O-CH_3$ | |
| $C_2H_5$ | $\bigcirc$ | |
| $\bigcirc-CH_2-$ | $\bigcirc$ | |
| $C_2H_5$ | $-\bigcirc H$ | |

Similar results are obtained with, e.g., the following amines: propylamine, isopropylamine, butylamine, isobutylamine, dibutylamine, diisobutylamine, triisobutylamine, aminohexane, aminoheptane, octylamine, dihexylamine, dipropylamine, diisopropylamine, methyldiisopropylamine, ethanolamine, methylethanolamine, dimethylethanolamine, aminoethanolamine, diethanolamine, methyldiethanolamine, triethanolamine, pyrrolidine, N-methylpyrrolidine, morpholine, methylmorpholine, ethylmorpholine, piperidine, ethylpiperidine, piperazine, methylpiperazine, cyclohexylamine, methylcyclohexylamine, dicyclohexylamine, methyldicyclohexylamine, aniline, methylaniline, dimethylaniline, urotropine, methoxyethylamine, di-2-methoxyethylamine, ethylenediamine, dimethylaminoethylamine, diethylaminopropylamine, hexamethylenediamine and triethylenediamine.

We claim:

1. A process for the manufacture of a salt of an O,S-dithiophosphoric acid diester of the formula:

of one another denote hydrogen or an organic radical, and $R^5$ and $R^6$ together with the nitrogen atom whose substituents they are may form a heterocyclic ring, which process comprises:

reacting an O,O,S-dithiophosphoric acid derivative of the formula:

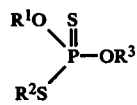

where $R^1$ and $R^2$ have the above meanings and $R^3$ denotes an organic radical,
with an amine of the formula:

$NR^4R^5R^6$ where $R^4$, $R^5$ and $R^6$ have the above meanings, said reaction being carried out in a solvent medium consisting essentially of water or water and an organic solvent which both dissolves in water and also dissolves the amine reactant.

2. A process as claimed in claim 1 using as amine at least twice the molar amount of a primary or secondary amine of the formula $$NR^4R^5R^6$$

where $R^4$ and $R^5$ independently of one another denote hydrogen or an organic radical, at least one of the radicals $R^4$ and $R^5$ denoting hydrogen and $R^6$ denotes an organic radical, and $R^5$ and $R^6$ together with the nitrogen atom whose substituents they are, may form a heterocyclic ring.

3. A process as claimed in claim 1 using as amine at least an equimolar amount of a tertiary amine of the formula $$NR^4R^5R^6$$

where $R^4$, $R^5$ and $R^6$ independently of one another denote an organic radical, and $R^5$ and $R^6$ together with the nitrogen atom whose substituents they are, may form a heterocyclic ring.

4. A process as claimed in claim 1 using a reaction mixture comprising an aqueous solution of an amine.

5. A process as claimed in claim 1 using a reaction mixture comprising water and a solubilizing agent as the organic solvent together with an amine which is sparingly soluble or insoluble in water.

6. A process as claimed in claim 1, wherein the reaction is carried out at a temperature of 0° C. to 60° C.

7. A process as claimed in claim 1, wherein $R^1$, $R^2$, and $R^6$ may be alkyl of 1 to 6 carbon atoms, alkenyl of 2 to 6 carbon atoms, alkynyl of 3 to 6 carbon atoms, alkoxyalkyl of 2 to 6 carbon atoms, alkylthioalkyl of 2 to 6 carbon atoms, phenyl which may be substituted by alkyl of up to 4 carbon atoms, halogen or haloalkyl, benzyl which may be substituted on the phenyl nucleus by alkyl of up to 4 carbon atoms, halogen or haloalkyl, or cycloalkyl of 6 to 8 carbon atoms, and $R^5$ and $R^6$, together with the nitrogen atom whose substituents they are, may form a heterocyclic ring having 6 members with the proviso that if either of $R^4$ or $R^5$ is not hydrogen, then it may have the same definition as set forth for $R^1$, $R^2$, and $R^6$.

* * * * *